United States Patent [19]

Moore

[11] Patent Number: 5,507,812
[45] Date of Patent: Apr. 16, 1996

[54] MODULAR PROSTHETIC LIGAMENT

[76] Inventor: David E. Moore, 346 E. 600 South, St. George, Utah 84770

[21] Appl. No.: 233,739

[22] Filed: Apr. 26, 1994

Related U.S. Application Data

[63] Continuation of Ser. No. 998,118, Dec. 28, 1992, abandoned.

[51] Int. Cl.$^6$ ......................................... A61F 2/08
[52] U.S. Cl. ............................................... 623/13
[58] Field of Search ................................. 623/11, 12, 13; 606/104

[56] References Cited

U.S. PATENT DOCUMENTS

| | | |
|---|---|---|
| 3,896,500 | 7/1975 | Rambert et al. . |
| 3,953,896 | 5/1976 | Treace . |
| 4,187,558 | 2/1980 | Dahlen et al. . |
| 4,301,551 | 11/1981 | Dore et al. . |
| 4,400,833 | 8/1983 | Kurland . |
| 4,467,478 | 8/1984 | Jurgutis . |
| 4,483,023 | 11/1984 | Hoffman, Jr. et al. . |
| 4,585,458 | 4/1986 | Kurland . |
| 4,590,928 | 5/1986 | Hunt et al. . |
| 4,597,766 | 7/1986 | Hilal et al. . |
| 4,605,414 | 8/1986 | Czajka . |
| 4,668,233 | 5/1987 | Seedhom et al. . |
| 4,712,542 | 12/1987 | Daniel et al. . |
| 4,728,329 | 3/1988 | Mansat . |
| 4,744,793 | 5/1988 | Parr et al. . |
| 4,755,183 | 7/1988 | Kenna . |
| 4,759,765 | 7/1988 | Van Kampen . |
| 4,772,286 | 9/1988 | Goble et al. . |
| 4,773,910 | 9/1988 | Chen et al. . |
| 4,775,380 | 10/1988 | Seedhom et al. . |
| 4,776,851 | 10/1988 | Bruchman et al. . |
| 4,790,850 | 12/1988 | Dunn et al. . |
| 4,792,336 | 12/1988 | Hlavacek et al. . |
| 4,795,466 | 1/1989 | Stuhmer et al. . |
| 4,804,383 | 2/1989 | Rey et al. . |
| 4,828,562 | 5/1989 | Kenna . |
| 4,834,752 | 5/1989 | Van Kampen . |
| 4,834,755 | 5/1989 | Silvestrini et al. . |
| 4,851,005 | 7/1989 | Hunt et al. . |
| 4,863,471 | 9/1989 | Manstat . |
| 4,870,957 | 10/1989 | Goble et al. . |
| 4,881,537 | 11/1989 | Henning . |
| 4,917,699 | 4/1990 | Chervitz . |
| 4,927,421 | 5/1990 | Goble et al. . |
| 4,932,972 | 6/1990 | Dunn et al. . |
| 4,942,875 | 7/1990 | Hlavacek et al. . |
| 4,946,377 | 8/1990 | Kovach . |
| 4,950,271 | 8/1990 | Lewis et al. . |
| 4,950,293 | 8/1990 | Beacon et al. . |
| 4,955,910 | 9/1990 | Bolesky . |
| 4,964,862 | 10/1990 | Arms . |
| 4,997,433 | 3/1991 | Goble et al. . |
| 5,002,574 | 3/1991 | May et al. ................... 623/13 |
| 5,004,474 | 4/1991 | Fronk et al. . |
| 5,024,669 | 6/1991 | Peterson et al. . |
| 5,026,398 | 6/1991 | May et al. . |

(List continued on next page.)

FOREIGN PATENT DOCUMENTS

| | | | |
|---|---|---|---|
| 2078528 | 1/1982 | United Kingdom | 623/13 |
| 9202196 | 2/1992 | WIPO | 606/104 |

*Primary Examiner*—Debra S. Brittingham
*Attorney, Agent, or Firm*—Thorpe North & Western

[57] ABSTRACT

A modular prosthetic ligament is disclosed for replacing a natural ligament which joins and allows articulation between adjacent ends of two bones. The prosthetic ligament includes a first anchor element, for disposition in the adjacent end of one of the bones, a second anchor element for disposition in the adjacent end of the other bone, and a cable assembly for interconnecting the first and second anchor elements. The cable assembly includes a hollow housing, one side of which is detachably joinable to the first anchor element, and the other side of which includes a slot through which one end of a cable is threaded to extend into the housing hollow. A ball or cylinder is disposed in the hollow of the housing and is coupled to the cable so that when the cable moves in the slot, the ball rolls or moves in the hollow of the housing. The other end of the cable is coupled to the second anchor element.

16 Claims, 1 Drawing Sheet

U.S. PATENT DOCUMENTS

| | | |
|---|---|---|
| 5,037,426 | 8/1991 | Goble et al. . |
| 5,061,283 | 10/1991 | Silvestrini . |
| 5,078,745 | 1/1992 | Rhenter et al. . |
| 5,092,887 | 3/1992 | Gendler . |
| 5,102,414 | 4/1992 | Kirsch . |
| 5,108,433 | 4/1992 | May et al. . |
| 5,151,104 | 9/1992 | Kenna ................ 623/13 |

MODULAR PROSTHETIC LIGAMENT

The present application is a continuation of U.S. patent application Ser. No. 07/998,118, filed on Dec. 28, 1992, now abandoned.

BACKGROUND OF THE INVENTION

This invention relates to prosthetic ligaments, and more particularly to a mechanical, modular prosthetic ligament.

Ligaments are flexible, fibrous cords or bands which join bones together and provide restraint to movement or articulation of one bone relative to another. With such movement, significant tensile forces are imposed on the ligaments and occasionally the result is a partial or complete rupture of the ligament. Attempts at repairing such ruptures by simply sewing the torn ends together are oftentimes not satisfactory because, among other things, many ligaments are not well vascularized and therefore do not heal by themselves. Frequently the geometry of the tear will not allow stable repair. This is often the case with severe damage to a ligament such as a complete rupture. Further, such a repaired ligament often does not afford the stability afforded by a healthy ligament and allows the bones being held together by the ligament to move in directions not normally allowed, causing either pain or undue wear on the bones, or both.

Other approaches which have been taken to correcting damaged ligaments include replacing the ligament with biological material (facia, tendon, other ligaments, etc.), with synthetic material ("ropes" made of various polymer compositions such as Gortex [registered trademark]), or with artificial prostheses known as ligament prostheses or prosthetic ligaments. The drawbacks of replacing a ligament with autograft biological material are that it is costly, risky, weakens the body part from which the substitute material is taken, and generally involves a long rehabilitation time. The use of allograft biological material (generally from a cadaver) carries additional risks of possible rejection, disease transmission (such as AIDS), as well as failure of the material due to processing. The principal drawback with the use of synthetic replacement material is that fatigue fracture generally occurs, involving the flaking off of parts of the synthetic material giving rise to particulate disease, and mechanical failure of the material.

As for the use of prosthetic ligaments, although they are generally designed to mimic the natural ligament through the use of flexible materials, they typically lack sufficient tensile strength, lack desired elasticity and flexibility, do not provide sufficient stability, and lack both durability and reliability.

SUMMARY OF THE INVENTION

It is an object of the invention to provide a prosthetic ligament which overcomes the drawbacks and disadvantages of the prior art approaches to correcting a damaged natural ligament.

It is also an object of the invention to provide a prosthetic ligament which is modularized to allow replacement of parts thereof without having to replace the entire prosthetic, and to allow tailoring the size of the prosthetic parts to the individual user.

It is a further object of the invention to provide a prosthetic ligament which is sturdy, durable reliable and unlikely to cause particulate disease.

It is still another object of the invention to provide such a prosthetic ligament which is relatively inexpensive and easy to manufacture.

It is also an object of the invention to provide such a prosthetic ligament which may be easily implanted in a person and which allows a relatively quick rehabilitation from the operation.

It is still a further object of the invention to provide a modular prosthetic ligament which functions similar to a natural ligament.

It is an additional object of the invention to provide such a prosthetic ligament which may be adjusted to vary the tension to which the joined bones are subjected.

The above and other objects of the invention are realized in a specific illustrative embodiment of a modular prosthetic ligament which includes a first anchor element for disposition in a bore or channel formed in the end of one of the bones to be joined, so that a portion of the first anchor element is accessible from said end, and a second anchor element for disposition in a bore or channel formed in the end of the other bone to be joined to the first bone, so that a portion of the second anchor element generally faces the accessible portion of the first anchor element. A cable assembly is provided for interconnecting the first and second anchor elements, with the cable assembly including a first end detachably joinable to the accessible portion of the first anchor element and pivotal therewith, a second end attached to the facing portion of the second anchor element and moveable longitudinally when under tension with respect to the facing portion, and a cable interconnecting the first end and second end, with the cable itself being laterally flexible and substantially inflexible longitudinally.

In accordance with one aspect of the invention, the first end of the cable assembly includes a hollow housing, one side of which is detachably joinable to the accessible portion of the first anchor element, and the other side of which includes a slot through which one end of the cable is threaded to extend into the housing hollow to move back and forth in the slot when urged to do so. The wall of the hollow at the other side of the housing has an arcuate concave surface to accommodate a body, at least a portion of whose surface is arcuately convex. The body is attached to one end of the cable so that as the cable moves back and forth in the slot, the arcuate surface of the body contacts and rolls over the arcuate surface of the hollow. Thus, the prosthetic ligament is articulated both to reduce stress on the cable material and to mimic the motion of a natural ligament.

In accordance with another aspect of the invention, the second anchor element includes an elongate hollow body having an opening in the facing portion leading to the hollow of the body, and a resilient means disposed in the hollow of a body. The second end of the cable extends through the opening in the hollow body and is attached to the resilient means to move under tension within the hollow.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
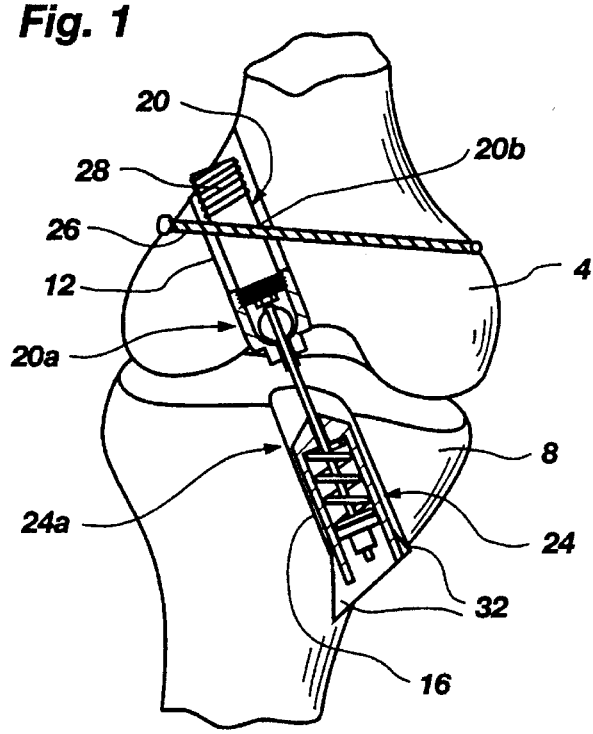
FIG. 1 is a diagrammatic, partially cross-sectional view of a modular prosthetic ligament made in accordance with the principles of the present invention, shown implanted in a knee joint as a prosthetic anterior cruciate ligament.

FIG. 1 shows diagrammatically a partially cross-sectional view of a modular prosthetic ligament installed or implanted to join, for example, the lower end of the femur bone 4 of a leg with the upper end of a tibia bone 8. The modular prosthetic ligament of FIG. 1 is implanted in a position in the femur 4 and tibia 8 as a replacement of the anterior cruciate ligament, a common ligament subject to rupture or other damage.

The modular prosthetic ligament of the present invention would be implanted, as shown in FIG. 1, by drilling an angularly positioned channel or bore 12 in the femur 4, and a generally aligned channel or bore 16 in the tibia 8. A femoral anchor 20 is then placed in the bore 12 to leave one end 20a exposed and accessible from between the femur 4 and tibia 8. A tibial anchor 24 is placed in the bore 16 with one end 24a facing the accessible end 20a of the femoral anchor 20. Exterior threads 28 are formed on the femoral anchor 20 for the purpose of securing the femoral anchor in place in the bore 12. In particular, the bore 12 would be formed with a diameter to allow the thread 28 to contact and grip the sides of the bore to secure the anchor in place. A transverse channel or bore 20b is formed in the femoral anchor 20, to receive a screw 26, which is screwed through one cortex of the femur bone 4, through the bore 20b and then through the other cortex of the femur bone 4. This further secures the femoral anchor 20 in place during initial insertion rehabilitation and healing.

Formed on the end of the tibial anchor 24 opposite the facing end 24a are splines 32 which are flared outwardly in a tapered fashion as shown from the exterior sides of the tibial anchor 24. (Alternatively, the end of the tibial anchor 24 could, itself, be formed to flare outwardly.) The tibial anchor 24 would be forced into the bore 16, with the splines 32 contacting and "digging into" the sidewalls of the bore to firmly secure the tibial anchor in place. However, the tibial anchor 24 can still be removed for repair or replacement if desired, by simply working the anchor 24 downwardly from the bore 16.

Figure 2:
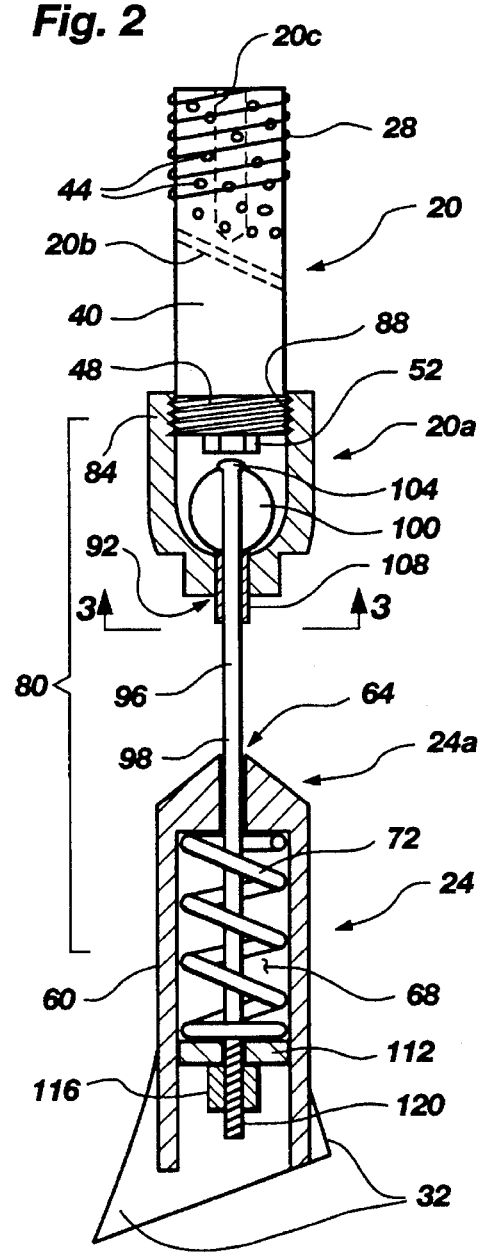
FIG. 2 is a side, elevational, partially cross-sectional view of the modular prosthetic ligament of FIG. 1.

There is shown in FIG. 2 a side, elevational, partially cross-sectional view of the modular prosthetic ligament of FIG. 1, in more detail. As there shown, the femoral anchor 20 includes a generally cylindrical body 40 made, for example, of chrome cobalt alloy. The threads 28 are formed on the upper end of the body 40 to enable screwing the body into a bore or channel formed in the femur 4 as described earlier. A plurality of holes or porosity 44 are formed to extend some distance into the body 40 at locations underlying the threads 28 to allow for bone ingrowth into the holes to better secure the femoral anchor 20 in place. A threaded axial bore 20c is formed in the upper end of the femoral anchor 20 for receiving a screw which may be used to pull and remove the femoral anchor if needed.

The lower end of the cylindrical body also includes threads 48 formed on the exterior thereof, and a drive nut (or alternatively it could be a notch) 52 formed on the lower end of the cylindrical body for use in screwing the body into the bore formed in the femur.

The tibial anchor 24 includes a hollow, generally cylindrical body 60 having an opening 64, axially disposed at the facing end 24a and leading from outside the body to the interior hollow 68 thereof. The lower end of the body 60 is also open, as indicated. The splines 32 as previously described are also shown extending laterally outwardly in a tapered fashion from the body 60.

Disposed in the hollow 68 is a coil spring 72. The spring 72 is oriented in the hollow 68 to flex longitudinally with the body 60 as will be further described later.

Figure 3:
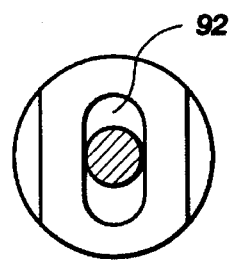
FIG. 3 is a bottom view of one of the anchor elements of the modular prosthetic ligament of FIG. 2 taken along lines 3—3.

Joining the femoral anchor 20 and tibial anchor 24 together is a cable assembly 80. This assembly includes a generally cylindrical hollow housing 84 open at an upper end and including interior threads 88 formed to be compatible with the threads 48 to allow screwing the housing 84 onto the lower end of the cylindrical body 40, as shown in FIG. 2. The lower end of the housing 84 includes a slot 92 (best seen in FIG. 3), through which a cable 96 is threaded.

The cable 96 is formed, for example, of chrome cobalt alloy to be flexible laterally but substantially inflexible longitudinally. One end of the cable 96 is attached to a ball 100 disposed in the hollow of the housing 84. Advantageously, the cable 96 is threaded through a diametric bore formed in the ball 100 and then an enlargement 104 formed at the upper end of the cable prevents the cable from pulling out of the diametric bore in the ball to thereby secure the ball in place on the end of the cable. A sleeve 108 is disposed about the cable 96 at the location that it passes through the slot 92 to serve as a protection against wear on the cable from moving back and forth in the slot and serve to reduce bending stress on the cable. The lower end of the hollow of the housing 84 is formed with an arcuate concave surface, as generally shown in FIG. 2, over which the ball 100 may move or roll as the cable 96 is moved in the slot 92. The radius of curvature of the ball 100 is the same as or less than the radius of curvature of the arcuate concave surface of the hollow of the housing 84, also as generally shown in FIG. 2. This allows the ball to move or roll freely in contact with the concave surface of the hollow.

The lower end of the cable 96 is joined end to end to a solid rod 98, of substantially the same diameter and the same material as the cable. The rod 98 passes through the bore 64 in the hollow body 60 of the tibial anchor 24 to extend axially through the coil spring 72 to a location below the coil spring. A washer 112 is disposed on the lower end of the rod 98 against the lower end of the coil spring 72, and held in place by a locking nut 116 which is screwed onto the lower end of the rod, over threads 120 formed on the rod. Thus, when the rod 98 is urged upwardly in the hollow body 60, the washer 112 is forced against the lower end of the coil spring 72, to tend to compress the spring and provide resistance to movement of the rod. In this manner, a tension is maintained in the rod 98 and thus the cable 96 and this tension can be adjusted by varying the longitudinal position of the washer 112 on the rod by simply screwing or unscrewing the locking nut 116 to the desired position on the end of the rod.

Advantageously, the hollow housing 84 and ball 100 are made of, for example, stainless steel or chrome cobalt alloy. The sleeve 108 might illustratively be made of chrome cobalt alloy. The hollow body 60 might illustratively be made of stainless steel. The coil spring 72 advantageously is made of stainless steel but could also be made of other metal alloys having similar properties.

With the prosthetic ligament described, two bones may be held together under a selectable tension and yet articulated movement between the bones is allowed. For example, movement such as occurs at a knee joint is allowed primarily by movement of the cable 96 in the slot 92 of the hollow housing 84 and the rolling or movement of the ball 100 over the arcuate concave surface of the hollow of the housing 84. That is, as the knee is bent, the angle between the femoral anchor 20 and the tibial anchor 24 is changed and this change is allowed because the cable 96 is allowed to move primarily only in one direction in the slot 92, with the rolling of the ball on the concave surface of the hollow of the housing 84. Such movement is free and yet a suitable stress is maintained on the cable by reason of the coil spring 72, to hold the femur and tibia securely together and allow for minor variations in the effective length of the prosthetic ligament. The cable 96 is also laterally flexible to further allow changing of the angle between the femoral anchor 20 and the tibial anchor 24. The articulation at the femur dissipates the bending stresses on the cable 96 (and other parts of the prosthetic ligament) to thereby substantially increase the fatigue life of the prosthetic ligament.

The prosthetic ligament of FIG. 2 is modular to allow disassembly of the different parts, and replacement thereof if necessary without having to dispose of the entire prosthetic. Thus, the hollow housing 84 may be unscrewed from the cylindrical body 40, the cable 96 may be removed both from the hollow housing 84 and the hollow body 60, and the coil spring 72 may likewise be removed and replaced from the hollow body 60. Various component sizes and spring tensions can be utilized to accommodate different patients.

Figure 4:
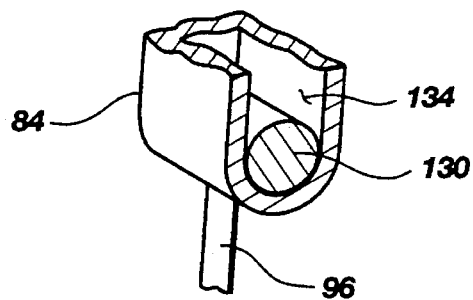
FIG. 4 is a partially cutaway, perspective view of an alternative embodiment of the cable coupling of the prosthetic ligament of the present invention.

FIG. 4 shows an alternative embodiment to use of the ball 100 by providing a cylinder 130 to roll or rotate in a cylindrical hollow 134 of a hollow housing 84. The cylinder 130 would be coupled to a cable 96 in a manner similar to the coupling of the cable to the ball 100, shown in FIG. 2.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A modular prosthetic ligament for replacing a natural ligament which joins and allows articulation between adjacent ends of a first bone and second bone comprising
   first anchor means for disposition in a bore formed in the adjacent end of the first bone so that a portion of the first anchor means is accessible from said adjacent end,
   second anchor means for disposition in a bore formed in the adjacent end of the second bone so that a portion of the second anchor means generally faces the accessible portion of the first anchor means, and
   a cable assembly for interconnecting the first and second anchor means, said cable assembly including
   a first end detachably joinable to the accessible portion of the first anchor means,
   a second end attached to the facing portion of the second anchor means and moveable longitudinally, when under tension, with respect to said facing portion, and
   cable means interconnecting the first end and the second end, said cable means being laterally flexible and substantially inflexible longitudinally, and being attached within the first end to pivot with respect to the first end at least in one direction substantially without bending of the cable means.

2. A modular prosthetic ligament as in claim 1 wherein said first end of the cable assembly comprises
   a hollow housing, one side of which is detachably joinable to the accessible portion of the first anchor means, and the other side of which includes a slot through which one end of the cable means is threaded to extend into the housing hollow and to move back and forth in the slot when so forced, the wall of the hollow at said other side of the housing having an arcuate concave surface, and
   body means, at least a portion of whose surface is arcuately convex, said body means being disposed in the housing hollow and attached to said one end of the cable means so that as the cable means moves back and forth in the slot, the arcuate surface of the body means contacts the arcuate surface of the hollow.

3. A modular prosthetic ligament as in claim 2 wherein said arcuate surfaces are generally spherical.

4. A modular prosthetic ligament as in claim 3 wherein the radius of curvature of the arcuate surface of the hollow is greater than that of the body means.

5. A modular prosthetic ligament as in claim 3 wherein the radius of curvature of the arcuate surface of the hollow is substantially the same as that of the body means.

6. A modular prosthetic ligament as in claim 2 wherein said arcuate surfaces are generally cylindrical.

7. A modular prosthetic ligament as in claim 2 wherein said slot is generally elongate, and wherein the width of the slot is just greater than the width of the cable means to prevent movement of the cable means laterally of the slot, while allowing movement longitudinally thereof.

8. A modular prosthetic ligament as in claim 7 further including a sleeve disposed about the cable means at the location it passes through the slot, to protect and prevent the cable means from contacting the walls of the slot and reduce bending stresses in the cable means.

9. A modular prosthetic ligament as in claim 2 wherein the accessible portion of the first anchor comprises a cylindrical end having exterior threads formed thereon, and wherein the one side of the hollow housing includes a cylindrical opening having interior threads formed therein which are compatible with said exterior threads, to enable screwing the threaded cylindrical opening onto the threaded cylindrical end of the first anchor.

10. A modular prosthetic ligament as in claim 2 wherein the cable means is made of chrome cobalt alloy.

11. A modular prosthetic ligament as in claim 1 wherein said body means is made of chrome cobalt alloy.

12. A modular prosthetic ligament as in claim 1 wherein said second anchor means comprises
   an elongate hollow body having an opening in said facing portion leading to the hollow of the body, and
   resilient means disposed in the hollow of the body,
   and wherein said second end of the cable assembly extends through the opening in said hollow body and is attached to said resilient means to move under tension within the hollow.

13. A modular prosthetic ligament as in claim 12 wherein said resilient means comprises a coil spring disposed coaxially in the hollow of the body, and wherein said cable assembly comprises
   an elongate laterally flexible and longitudinally inflexible cable, the second end of which extends axially through the center of the coil spring, and stop means disposed on said second end of the cable to contact and compress the coil spring when the cable is pulled outwardly from the body.

14. A modular prosthetic ligament as in claim 13 wherein said coil spring is made of a biocompatible metal alloy.

15. A modular prosthetic ligament as in claim 12 further including one or more splines which extend radially outwardly from the body at the end rearwardly of the facing portion of the body.

16. A modular prosthetic ligament as in claim 1 wherein said cable assembly further includes means for selectively adjusting the position of said second end to the facing portion of said second anchor means to thereby adjust the resistant tension of the second end, when under tension.

* * * * *